United States Patent [19]

Baranowska-Kortylewicz

[11] Patent Number: 5,468,853
[45] Date of Patent: Nov. 21, 1995

[54] SYNTHESIS OF 5-RADIOHALO-2'-DEOXYURIDINE

[75] Inventor: Janina Baranowska-Kortylewicz, Omaha, Nebr.

[73] Assignee: Board of Regents University of Nebraska, Lincoln, Nebr.

[21] Appl. No.: 176,146

[22] Filed: Dec. 30, 1993

[51] Int. Cl.$^6$ .................. C07H 19.073; C07H 19/10; A61K 31/70
[52] U.S. Cl. .................. 536/28.55; 514/50; 536/55.3
[58] Field of Search .................. 536/28.55, 55.3

[56] References Cited

U.S. PATENT DOCUMENTS 4,851,520  7/1989  Kassis et al. .................. 536/28.55

OTHER PUBLICATIONS

Wigerinck et al. J. Med. Chem. 36:538–543, 1993.
Baranowska–Kortylewicz, et al., *Radioiodomercuration: a Simple Synthesis of 5–[$^{123/125/127}$I]Iodo–2'–Deoxyuridine*, Appl. Radiat. Isot. vol. 39, No. 4, pp. 335–341, 1988.
Bakker, et al., *The Electrophilic Iodination with $^{131}$I of $N_1$–substituted Uracils Using Chloramine–T as Oxidant*, Int. J. Radiat. Appl. Radiat. Isot. vol. 32, pp. 176–178, 1981.
Keough, et al., *An Improved Method for Synthesis and Purification of $^{125}$I or $^{131}$I Labeled Carrier–Free 5–Iodo–2'–Deoxyuridine*, J. of Labelled Comp. and Radipharmaceuticals, vol. XIV, No. 1, pp. 83–90, 1978.

Primary Examiner—Douglas W. Robinson
Assistant Examiner—Gary L. Kunz
Attorney, Agent, or Firm—Henderson & Sturm

[57] ABSTRACT

Method of synthesizing 5-radio-halogenated-2'-deoxyuridine from 5-trimethylstannyl-2'-deoxyuridine is described. The method consists of the steps of mixing 5-trimethylstannyl-2'-deoxyuridine with an aqueous solution consisting of a radiohalide and NaOH to form a first mixture, adding $H_2O_2/CH_3COOH$ to the first mixture to form a second mixture, sonicating the second mixture, evaporating the solvent from the second mixture to form a residue, reconstituting the residue, filtering the residue; and then purifying the filtered residue such that at least one of a radiohalogenated nucleoside and nucleotide is obtained. A kit consisting of the components required for the above synthesis is also described.

18 Claims, 2 Drawing Sheets

SYNTHESIS OF 5-RADIOHALO-2'-DEOXYURIDINE

GOVERNMENT RIGHTS

The present invention was privately funded. The government has no rights in the present invention.

CROSS REFERENCES

RELATED APPLICATIONS

The present application is an original patent application and is currently not known to be related to any co-owned and co-pending application.

TECHNICAL FIELD

The present invention is generally related to a method of making radiohalogenated nucleotides and nucleosides and more particularly to a novel method of preparing 5-radiohalogenated-2'-deoxyuridines.

BACKGROUND ART

Radiohalogenated nucleosides and nucleotides are currently utilized as diagnostic and therapeutic agents, cell labeling agents, radiolabeling agents for oligonucleotides, and the like. One radiohalogentated compound of particular importance is 5-radioiodo-2'-deoxyuridine (IUdR).

The synthesis and biological activity of iododeoxyuridine was first described by Prusoff in 1959 (Biochem. Biophys. Acta 33:295–296). Prusoff's synthesis is still utilized, both with and without modification, and involves the reaction of UdR with sodium radioiodide in nitric acid (*J. Labelled Comp. Radiopharm.* 14:83–90(1978); *CancerRes.* 21:345–352(1960); *J. Nucl. Med.* 34:1152–1162(1983); *Int. J. Appl. Radiat. Isot.* 36:176–181(1981)).

While the Prusoff method established the art and paved the way for improved methods of synthesis, it and other methods relying on electrophilic substitution, are complicated and lengthy procedures which produce several radiolabeled by-products, limited overall yields (≈50%), and low specific activity (due to unidentified uv-absorbing impurities).

Another more widely utilized method of IUdR syntheses is based on a radiohalodemercuration reaction (U.S. Pat. No. 4,851,520, *Appl. Radiat. Isot.* 39:335–341(1988)). This method produces higher overall yields of no-carrier-added product. However, because of the nature of the precursor, the crude IUdR recovered form the reaction mixture is contaminated with trace amounts of mercury (up to 200 ppm) and requires further purification before it may be provided to humans.

The increased demand for clinically acceptable $^{123/125}$IUdR preparations has prompted those skilled in the at to investigate other methods of synthesis which might be utilized to rapidly prepare high quality, sterile, and no-carrier-added radio-IUdR. Here-to-before, these attempts have failed. Such failures are primarily due to the underlying complexity of the problem, for example, the short reaction time required for compatibility with short-lived radioisotopes ($^{123}$I) and the difficulty of purification to obtain a suitable product.

OBJECTS OF THE INVENTION

Thus, it is a primary object of the present invention to provide a method of making radiohalogenated nucleosides and nucleotides which have a radiochemical yield of at least ninety percent and a radiochemical purity of at least ninety percent.

Another object of the present invention is to provide a method of making radiohalogenated nucleosides and nucleotides which may be accomplished rapidly such that short-lived radioisotopes such as iodine-123, astatine-211, and bromine-80 m may be prepared.

Still another object of the present invention is to provide a method of making radiohalogenated nucleosides and nucleotides which utilizes a stable starting material which may be used with a number of solvents such that a number of radiolabeled derivatives may be prepared.

Yet another object of the present invention is to provide a method of making radiohalogenated nucleosides and nucleotides which does not produce a final product containing heavy metals.

Yet still another object of the present invention is to provide a method of making radiohalogenated nucleosides and nucleotides which may be utilized to make compounds of any desired specific activity.

Yet still a further object of the present invention is to provide a method of making radiohalogenated nucleosides and nucleotides which may be utilized on-site in kit form.

Finally, it is an object of the present invention to provide a method of making radiohalogenated nucleosides and nucleotides which may be utilized: (1) to replace P-labelled nucleosides and nucleotides in molecular biology; (2) in cell survival, cell division delay, and S-phase marker tissue culture studies; (3) in the diagnostic assessment of tumor progression and proliferation activity studies; (4) as a prognostic agent in evaluating chemo- and radio- therapies; and (5) as a therapeutic agent for a variety of tumors (with Auger electron emitters) such as (a) brain tumors (glioma multiforme, primary CNS lymphomas, and astrocytomas), (b) colorectal cancer (primary and liver metastasis), (c) bladder cancer (all stages of transitional cell carcinomas), (d) breast cancer, and (d) ovarian cancer.

DISCLOSURE OF THE INVENTION

A rapid, simple and inexpensive synthesis of 5-radiohalogenated-2'-deoxyuridine from 5-trimethylstannyl-2'-deoxyuridine is described. The total reaction and purification time including thin layer chromatography (tlc) for quality control is less than 30 min. This method produces overall yields of greater than ninety-five percent (>95%) of $^{123}$I-, $^{125}$I-, $^{131}$I-UdR. The radiochemical purity of all tested preparations (>20) has been determined to be greater than 99%. This novel method is also the basis of a radiolabeling kit/generator for preparation of radiohalogenated nucleosides. 2'-Deoxyuridine (UdR) halogenated with a stable isotope of bromine has also been synthesized establishing that the method may be applied to the preparation of 5-radiobromo-2'-deoxyuridine (BUdR).

MODES FOR CARRYING OUT THE INVENTION

Synthesis of radioiodinated 5-iodo-2'-deoxyuridine was first described by Prusoff et al. in 1959. This method has been used extensively with and without modifications (*J. Labelled Comp. Radiopharm.* 14:83–90; *Cancer Res.* 21:345–352; *J. Nucl. Mad.* 34:1152–1162; *Int. J. Appl. Radiat. Isot.* 36:176–181(1981)). The Prusoff method involves the reaction of UdR with sodium radioiodide in nitric acid or in the presence of other strong oxidants. In addition to IUdR several radiolabeled byproducts are generated reducing the overall yield of IUdR to about 50%. The specific activity is frequently lowered by uv-absorbing unidentified impurities (*J. Nucl. Med.* 34:1152–1162; *Int. J. Appl. Radiat. Isot.* 36:176–181(1981)). A newer method of IUdR synthesis is based on the radiohalodemercuration re-action (U.S. Pat. No. 4,851,520, *Appl. Radiat. Isot.* 39:335–341). This procedure provides high overall yields of no-carrier-added products. However, because of the nature of the precursor, IUdR recovered from the reaction mixture is contaminated with trace amounts of mercury compounds of an unspecified nature (up to 200 ppm). Thus, without purification it may not be utilized in humans.

The increased demand for clinically acceptable $^{123/125}$IUdR preparations (*J. Nucl. Med.* 34:1175–1183(1993); *Eur. Assoc. of Nucl. Med. Con.* Laussane, Oct. 10–14, (1993); *Eur. J. Clin. Invest.* 22:A23(1992); *Clin. Res.* 40:422A(1992); *Cancer Treat. Rev.* 14:397–399(1987); *J. Nucl. Med.* 34:37P(1993)) prompted the development of the present invention which may be utilized as a simple and rapid synthetic method for utilization as a radiolabeling kit. Such a kit allows production, on demand and on site, of a high quality, sterile, and no-carrier-added radio-IUdR. Two of the main considerations were: (a) the reaction time compatible with short-lived radioisotopes (i.e. $^{123}$I), and (b) the ease of purification of the final product. The application of trimethylstannyl precursors has established a rapid, novel synthetic method leading to no-carrier-added, high specific activity nucleosides and nucleotides.

A. Results and Discussion

Figure 1:
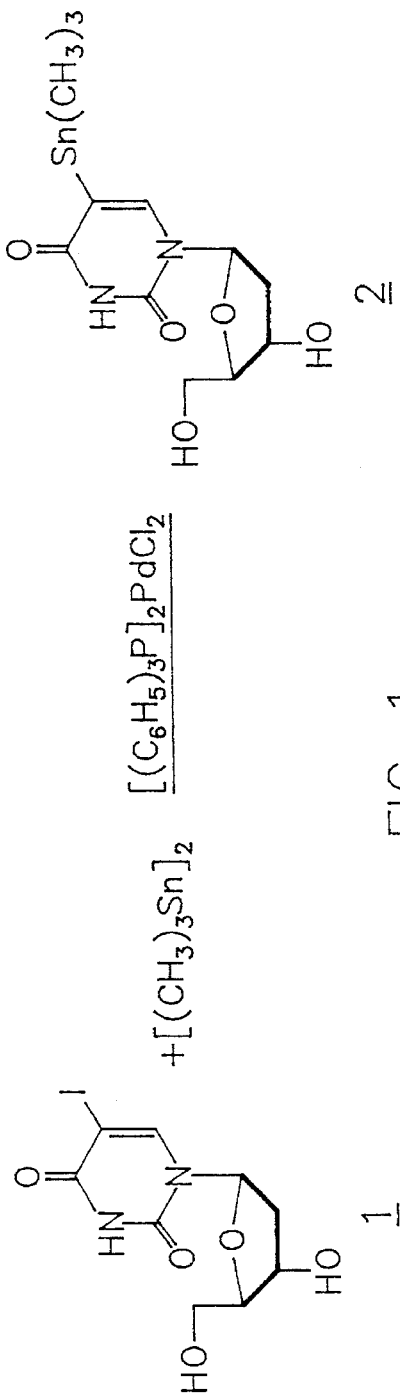
FIG. 1 is a reaction diagram illustrating the preparation of 5-trimethyl-stannyl-2'-deoxyuridine.

5-Trimethylstannyl-2'-deoxyuridine 2 was synthesized from IUdR 1 using the modified method of Wigerinck et al. (*J. Med. Chem.* 36:538–543(1993)) as shown in FIG. 1. The stannyl precursor was purified on a flash silica gel column. Analytical samples were further purified on a normal phase high pressure liquid chromatography (hplc) column. The stability of the stannyl precursor was tested under a variety of conditions. The $CHCl_3$ solution of 2 is stable for up to 6 months (longest period tested) when stored at −20° C. under a nitrogen atmosphere. The precursor 2 also appears to be stable when held in a solid form in a tightly capped test tube. The method has provided yields of greater than ninety-five percent (>95%) of radio-IUdR even after prolonged storage (7 months).

Figure 2:
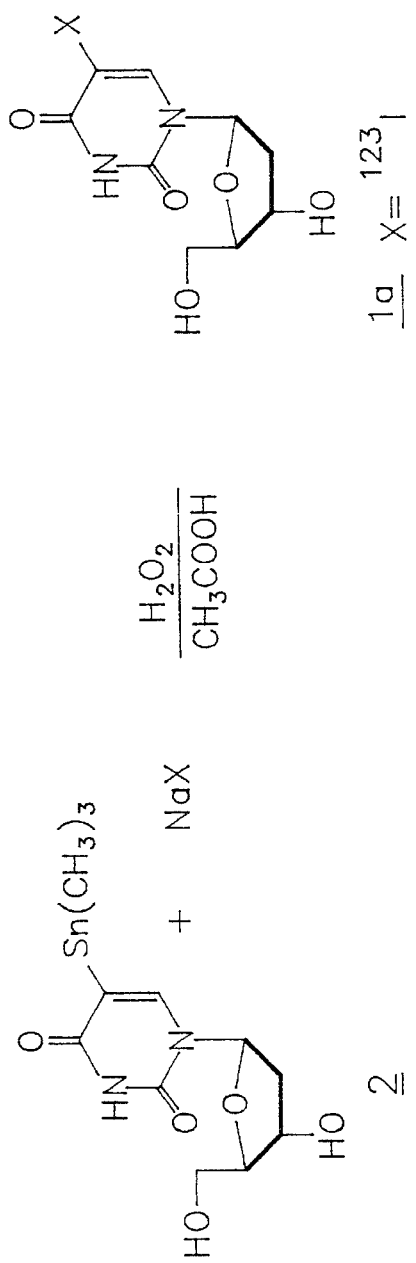
FIG. 2 is a reaction diagram illustrating the preparation of radio-IUdR from 5-trimethylstannyl-2'-deoxyuridine.
Figure 3:
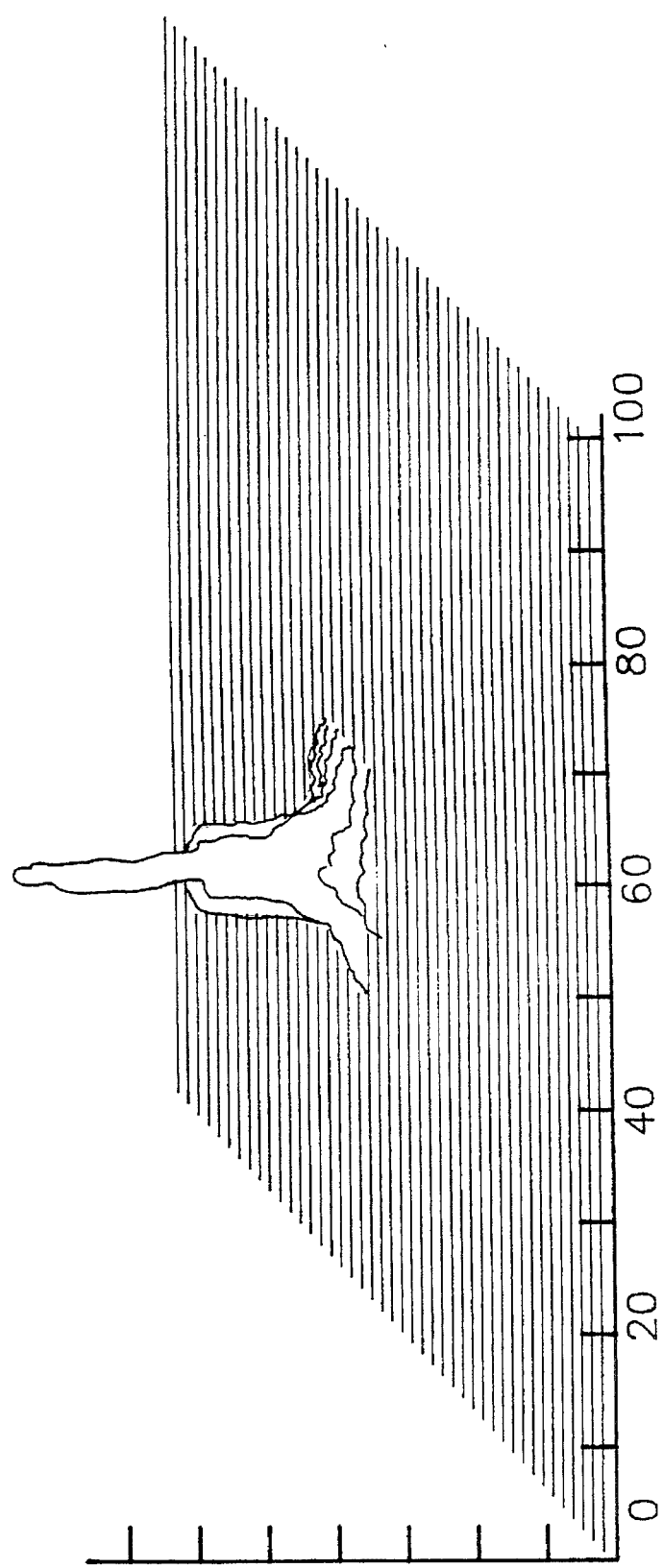
FIG. 3 is a radioactivity scan of a two-dimensional tlc silica gel plate of the reaction mixture of the present invention containing $^{123}$IUdR. A sample of $^{127}$IUdR spotted with the reaction mixture indicates that the radioactivity co-migrates with the uv-absorbing spot (origin at 0 mm horizontal, solvent front at 90 mm in both directions, eluted in 8:1 $CH_2Cl_2/CH_3OH[v/v]$).

The reaction conditions for the preparation of the halogenated derivatives were perfected using sodium [$^{127}$I] iodide. The synthesis is outlined in FIG. 2. The reaction was conducted in either chloroform as a solvent or in a heterogenous mixture using test tubes coated with 2. The complete depletion of iodine was observed in both cases. The reaction time for the heterogenous mixture was just a few seconds longer than for the reaction run in chloroform (60 sec versus 15 sec). The use of 25% hydrogen peroxide in glacial acetic acid (v/v) as the oxidant simplified the purification of the final halogenated deoxyuridine (radio-IUdR, BUdR). The product was isolated on a small, reversed-phase cartridge (about 0.1 mL dry volume of a $C_{18}$ packing in a 1-mL syringe). Filtration through a 0.2 µm sterilization filter also removed all detectable uv-absorbing contaminants. The hplc analysis of the filtered reaction mixture (either $^{123}$I or $^{125}$I labeling; aliquots from reactions with 1 mCi to 15 mCi of radioiodide) using dual detection at 254 and 280 nm with the sensitivity set at 0.05 absorbance units (AU) failed to reveal any products other than the desired IUdR (radioactivity detected in fractions with the retention time [$R_T$] corresponding to that of IUdR standard). The tlc analysis (uv at 254 nm and radioactivity detection) indicated the presence of a single radioactive spot co-migrating with the authentic sample of $^{127}$IUdR (FIG. 3). More than 20 lots of no-carrier-added $^{123}$I-, $^{125}$I-, and $^{131}$I-UdR were prepared with approximately a 95% yield. The analysis of crude reaction mixtures revealed that in all cases the conversion of radioiodide into radio-IUdR went to completion (100%). The yield of recovery of IUdR was always about 95% due to the losses during transfer of the reaction mixture and the sterilization process. Similar results were obtained during the preparation of 5-bromo-2'-deoxyuridine. The reaction of molar equivalents of 2 and sodium bromide produced pure BUdR with a 92% yield.

The efficiency of this method also allows for the establishment of a set of radiolabeling conditions compatible with a rapid and facile "kit" preparation of IUdR in a clinical setting. This is particularly important in the case of $^{123}$IUdR because of the short half-life (13 h) of $^{123}$I. The "kit" contains a test tube coated with 100 µg of 5-trimethylstannyl-2'-deoxyuridine, a vial with the oxidant (such as $H_2O_2/CH_3COOH$, 1:3, v/v; Iodogen; or Chloramine-T; or the like), a syringe-$C_{18}$-cartridge equipped with a 0.2 µm sterile filter, tlc plates pre-loaded with a standard ($^{127}$IUdR), and a vial with tlc developing solvents for quality control testing. The reliability and simplicity of this method allow for routine preparations of high activities of IUdR with minimal radioactive exposure.

An "IUdR generator" has also been made by utilizing the reaction mixture containing (10 mCi of $^{123}$IUdR)loaded onto a $C_{18}$ Sep-Pak® cartridge (1 mL of dry packing) and eluted daily with 1 mL of saline. Each collected fraction may be analyzed for IUdR. The recovery of IUdR was 91% with about 2.2 mCi collected in the first elution and from 1.7 to 1.8 mCi in each of the four consecutive elutions (corrected for decay). Isolated fractions contained only radiolabeled IUdR. The elution of a similarly prepared cartridge containing 5 mCi $^{125}$IUdR yielded over 90% of the product collected in 0.25 mL of saline daily for 9 days (about 0.5 mCi per elution).

Experimental

Materials: All chemicals and solvents were from Aldrich Chemical Company (Milwakee, Wis.). Iodine-123 was purchased from Nordion (Kanata, Canada), iodine-125 and iodine-131 from either Amersham (Arlington Heights, Ill.), ICN (Costa Mesa, Calif.), or Du Pont NEN Research Products (Boston, Mass.). $^{123}$I and $^{125}$I were no-carrier-added with specific activities of about 230,000 Ci/mmol and 2,100 Ci/mmol, respectively. $^{131}$I had a specific activity of 790–1570 Ci/mmol. Na$^{123}$I was provided as a solid containing known amounts of NaOH, other radioisotopes were provided as sodium radioiodide solutions in NaOH. Hplc analyses of radioactive products were made using a C$_{18}$ column (4.6×250 mm; Vaydac, Hesperia, Calif.) with either isocratic 80/20 H$_2$O/CH$_3$OH (15 min) followed by linear gradient to 100% CH$_3$OH (30 min) or isocratic 95/5 H$_2$O/CH$_3$CN as the elution solvents. The normal phase columns were from Phenomenex (4.6×250 mm and 22.5×250 mm; Maxsil 10 Silica; Torrance, Calif.). Tlc plates were silica gel on plastic backing with uv indicator (EM Science, Gibbstown, N.J.). The radioactivity of hplc fractions was measured in a Packard Cobra II gamma counter. Tlc plates were scanned using a gas-flow Vista 100 analytical, digital imaging system (Radiomatic, Meriden, Conn.). Proton nmr spectra were recorded using a Varian XL 300 spectrometer.

5-(Trimethylstannyl)-2'-deoxyuridine: 5-Iodo-2'-deoxyuridine 1 ( 1 g, 2.8 mmol) was dissolved in 45 mL anhydrous dioxane at about 60° C. The mixture was cooled to room temperature and 50 mg of bis(triphenylphosphine)palladium(II) dichloride and 2 g (6.1 mmol) of hexamethylditin were added. The mixture was refluxed until tlc indicated that all of IUdR reacted (about 5 h). The solution was cooled to 40° C. and the solvent evaporated to dryness on a rotary evaporator. The dark brown, solid residue was loaded on a silica flash column and eluted with a 92:8 (v/v) mixture of CHCl$_3$/CH$_3$OH. Fractions containing the product were combined and evaporated to dryness. The trimethylstannyl derivative 2 was recovered in 54% yield (0.6 g) as a colorless oil. $^1$Hnmr (CDCl$_3$/DMSO-d$_6$) 0.68 (s, 9 H, [CH$_3$]$_3$SN); 2.57 (m, 1H, HC2'); 4.05 (t, 2H, HC5'); 4.27 (m, 1H, HC4'); 5.43 (t, 1H, C5'-OH); 5.66 (d, 1H, C3'-OH); 6.64 (t, 1H, HC1'); 8.15 (s, 1H, HC6); 11.54 (s, 1H, HN3).

5-Iodo-2'-deoxyuridine: The same procedure was used for all radioactive isotopes. The reactions with $^{127}$I or a carrier-added $^{125}$I were carried out on a larger scale (≈100 times) to allow for a detailed analysis of the reaction mixture and final products. All syntheses involving radioisotopes of iodine were conducted behind a lead-lined screen in a well-ventilated fume hood equipped with charcoal filters. To a solution of 10–100 μg 2 in 100 μL chloroform was added 1–30 mCi of sodium radioiodide in 0.1 N NaOH (up to 50 μL). The mixture was briefly mixed and 1–5 μL of H$_2$O$_2$/CH$_3$COOH (1:3; v/v) was added (other oxidants may also be utilized, e.g., Iodogen, or Chloramine-T and the like). The two-layer reaction mixture was sonicated for 15 sec and three 0.5-μL portions were spotted on silica gel plates to determine the progress of radioiodination. The radioactive spots were measured with a Vista 100 radioactivity scanner; the uv absorbing spots were visualized with a hand-held uv lamp (254 nm). In all cases all of radioiodine was converted into IUdR in less than 15 sec.

The work-up of the reaction mixture was as follows: chloroform was evaporated to dryness under a stream of nitrogen and 1 mL of the desired solvent (saline, 0.05 M phosphate-buffered saline, pH 7.2 [PBS]; double-distilled water) was added to the residue. The radioactive content of this solution was measured in a dose calibrator (Capintec). In the initial studies each 1-mL solution was divided into two portions to determine the efficiency of the purification process and to identify any source of radioactivity losses. One part was passed through a C$_{18}$ cartridge and a 0.2 μm filter whereas the second fraction was only filtered through a 0.2 μm sterile filter. The C$_{18}$ cartridge was washed prior to the purification step with methanol (the equivalent of ten void volumes of the cartridge), followed by ten void volume equivalents of distilled water and three of the elution solvent (saline, PBS, or water). The radioactive content of collected filtrates was determined in a gamma counter and the mixture was analyzed on tlc plates (CH$_2$Cl$_2$/CH$_3$OH 8:1, v/v, R$_f$: free iodide 0.1, IUdR 0.45, UdR 0.3, SnUdR 0.7; or 1-butanol saturated with concentrated ammonia, R$_f$ free iodide 0.7, IUdR 0.5) and on a C$_{18}$ reversed phase column (flow rate 1 mL/min; CH$_3$OH/HO$_2$O isocratic 80/20 [v/v] for 10 min with the linear gradient to 100% CH$_3$OH at 10 min, retention times [R$_T$]: free iodide 3 min, UdR 4.5 min, IUdR 8 min, SnUdR 22 min; or CH$_3$CN/H$_2$O 95:5 [v/v], R$_T$ free iodide 3 min, UdR 12 min, IUdR 20 min). For radioactive preparations the uv detector was set at 0.05 AU and 1-mL fractions were collected. The radioactive content of each fraction was determined in a gamma counter. To verify the identity of the radioactive product hplc and tlc analyses were performed using samples containing known quantities of $^{127}$IUdR, $^{127}$, UdR, and SnUdR 2. The reactions conducted in the absence of chloroform were treated as described above but the sonication of the reaction mixture was extended to 60 sec. In all cases the conversion of iodide into IUdR was complete. The yield of IUdR recovery was always over 90% ( usually 95% or more).

A heterogenous mixture may also be prepared by adding 1–100 μg of stannyl precursor in chloroform to a test tube. The solvent is then evaporated to dryness (e.g., gently heat or stream of nitrogen) and 10–100 μL of water is added with sodium radioiodide and 1–5 μL of an oxidant (e.g., H$_2$O/CH$_3$COOH, Iodogen, Chloramine-T, or the like). The resulting mixture is then sonicated briefly (30–60 s), additional solvent is added, and the mixture is filtered (e.g., sterile filter or C$_{18}$ cartridge).

Generator

Generator. The reaction mixture containing 10 mCi of $^{123}$IUdR was loaded onto a C$_{18}$ Sep-Pak® cartridge (1 mL of dry packing) and eluted daily with 1 mL of saline. Each collected fraction was analyzed for IUdR. The recovery of IUdR was 91% with about 2.2 mCi collected in the first elution and from 1.7 to 1.8 mCi in each of the four consecutive elutions (corrected for decay). Isolated fractions contained only radiolabeled IUdR. The elution of a similarly prepared cartridge containing 5 mCi $^{125}$IUdR yielded over 90% of the product collected in 0.25 mL of saline daily for 9 days (about 0.5 mCi per elution).

It will be apparent to those skilled in the art that the teachings of the present invention may be adapted and utilized in the preparation and use of other radiohalogenated nucleosides and nucleotides.

I claim:

1. A method of preparing 5-radiohalo-2'-deoxyuridine or 5'-nucleotides thereof, comprising:

(a) mixing 5-trimethylstannyl-2'-deoxyuridine with an aqueous solution consisting of a radiohalide selected from the group consisting of radioiodide, radiobromide and radioastatine, and NaOH to form a first mixture at a temperature between about 0° C. and about 37° C.;

(b) adding an oxidant to said first mixture to form a second mixture, wherein said oxidant is selected from the group consisting of H$_2$O$_2$/CH$_3$COOH, Iodogen and Chloramine-T.

(c) sonicating the second mixture;

(d) evaporating at room temperature the solvent from said second mixture by using a stream of inert gas or air to form a residue;

(e) reconstituting the residue;

(f) filtering said residue;

(g) purifying the filtered residue on a reversed phase medium to yield said 5-radiohalo-2'-deoxyuridine or 5'-nucleotides thereof.

2. The method of claim 1 wherein second mixture is sonicated for approximately 15 seconds.

3. The method of claim 1 wherein the residue is reconstituted in a medium suitable for injection.

4. The method of claim 3 wherein said medium suitable for injection consists essentially of $H_2O$.

5. The method of claim 1 wherein said filtration step is accomplished by passing the residue through a syringe plugged with glass wool and filled with 0.2 mL of a $C_{18}$ support.

6. A method of preparing 5-radiohalo-2'-deoxyuridine or 5'-nucleotides thereof, comprising:

(a) mixing 5-trimethylstannyl-2'-deoxyuridine with chloroform to form a first mixture;

(b) depositing said 5-trimethystannyl-2'-deoxyuridine in a vial by evaporation of said chloroform;

(c) adding a radiohalide, an oxidant, and an equal volume of aqueous acetic acid to form a second mixture;

(d) sonicating the second mixture for less than 20 seconds;

(e) evaporating said chloroform under a stream of inert gas or air;

(f) filtering said sonicated mixture through a filter to obtain the 5-radiohalo-2'-deoxyuridine or 5'-nucleotides thereof.

7. The method of claim 6 wherein between 1 and 100 μg of 5-trimethylstannyl-2'deoxyuridine is utilized.

8. The method of claim 6 wherein said evaporation is accomplished via a stream of inert gas or air.

9. The method of claim 6 wherein between 10–100 μL water is utilized.

10. The method of claim 6 wherein said oxidant is $H_2O_2/CH_3COOH$, Iodogen, or Chloramine-T.

11. The method of claim 6 wherein said second mixture is sonicated for approximately 45 seconds.

12. The method of claim 11 wherein said filtration is accomplished via at least one of a sterile filter and a $C_{18}$ cartridge.

13. A kit, comprising:

(a) a test tube coated with 5-trimethylstannyl-2'-deoxyuridine;

(b) a vial containing an oxidant;

(c) a $C_{18}$ cartridge having a filter; and (d) tlc plates pre-loaded a standard selected from the group consisting of 5-radiohalo-2'-deoxyuridine and 5'-nucleotides thereof.

14. The kit of claim 13 further comprising a vial with tlc developing solvents for quality control.

15. A method of preparing 5-radiohalo-2'-deoxyuridine and 5'-nucleotides thereof, comprising:

(a) mixing 5-trimethylstannyl-2'-deoxyuridine with an aqueous solution consisting of a radiohalide selected from the group consisting of radioiodide, radiobromide and radioastatine, and NaOH to form a first mixture at a temperature between about 0° C. and about 37° C.;

(b) adding an oxidant to said first mixture to form a second mixture, wherein said oxidant is selected from the group comprising $H_2O_2/CH_3COOH$, Iodogen and Chloramine-T.

(c) sonicating the second mixture;

(d) evaporating at room temperature the solvent from said second mixture by using a stream of inert gas or air to form a residue;

(e) reconstituting the residue; and (f) filtering said residue to yield said radiohalogenated nucleoside or nucleotide.

16. The method of claim 15 wherein second mixture is sonicated for approximately 15 seconds.

17. The method of claim 15 wherein the residue is reconstituted in a medium suitable for injection.

18. The method of claim 15 wherein said medium suitable for injection consists essentially of $H_2O$.

\* \* \* \* \*